United States Patent [19]
Bryan et al.

[11] Patent Number: 5,865,846
[45] Date of Patent: Feb. 2, 1999

[54] HUMAN SPINAL DISC PROSTHESIS

[76] Inventors: Vincent Bryan, 4624 E. Mercer Way, Mercer Island, Wash. 98040; Alex Kunzler, 4422 140th, SE., Bellevue, Wash. 98002

[21] Appl. No.: 856,513

[22] Filed: May 15, 1997

Related U.S. Application Data

[60] Division of Ser. No. 681,230, Jul. 22, 1996, Pat. No. 5,674,296, which is a continuation-in-part of Ser. No. 339,490, Nov. 14, 1994, abandoned.

[51] Int. Cl.⁶ .......................................................... A61F 2/44
[52] U.S. Cl. ................................. 623/17; 606/61; 606/86; 606/87
[58] Field of Search .......................... 623/16, 17; 606/60, 606/61, 72, 73, 86, 87

[56] References Cited

U.S. PATENT DOCUMENTS

| | | | |
|---|---|---|---|
| 2,677,369 | 5/1954 | Knowles | 623/17 |
| 4,599,086 | 7/1986 | Doty | 616/61 X |
| 4,911,718 | 3/1990 | Lee et al. | 623/17 |
| 4,932,969 | 6/1990 | Frey et al. | 623/17 |
| 4,997,432 | 3/1991 | Keller | 623/17 X |
| 5,192,326 | 3/1993 | Bao et al. | 623/17 |
| 5,246,458 | 9/1993 | Graham | 606/87 X |
| 5,370,697 | 12/1994 | Baumigartner | 123/17 |
| 5,556,431 | 9/1996 | Buttrer-Janz | 623/17 |
| 5,674,294 | 10/1997 | Bainville et al. | 623/17 |

*Primary Examiner*—Mary Beth Jones
*Attorney, Agent, or Firm*—Hill & Simpson

[57] ABSTRACT

The invention relates to a spinal disc endoprosthesis. The endoprosthesis has a resilient body formed of one or more materials which may vary in stiffness from a relatively stiff exterior annular gasket portion to a relatively supple central nucleus portion. Concaval-convex elements at least partly surround that nucleus portion so as to retain the nucleus portion and gasket between adjacent vertebral bodies in a patient's spine. Assemblies of endoprosthetic discs, endoprosthetic vertebral bodies, and endoprosthetic longitudinal ligaments may be constructed. To implant this endoprosthesis assembly, information is obtained regarding the size, shape, and nature of a patient's damaged spine. Thereafter, one or more prosthetic vertebral bodies and disc units are constructed in conformity with that information. Finally, the completed and conformed vertebral body and disc assembly is implanted in the patient's spine.

9 Claims, 10 Drawing Sheets

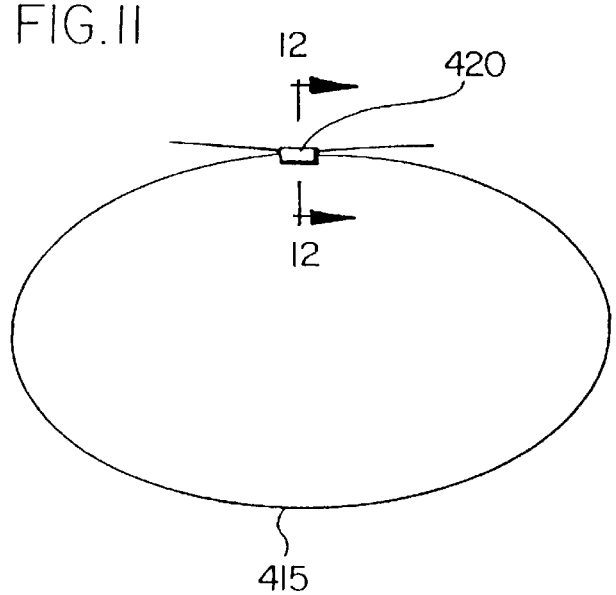
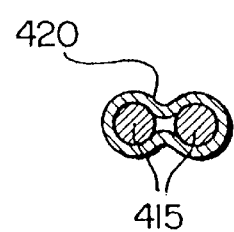
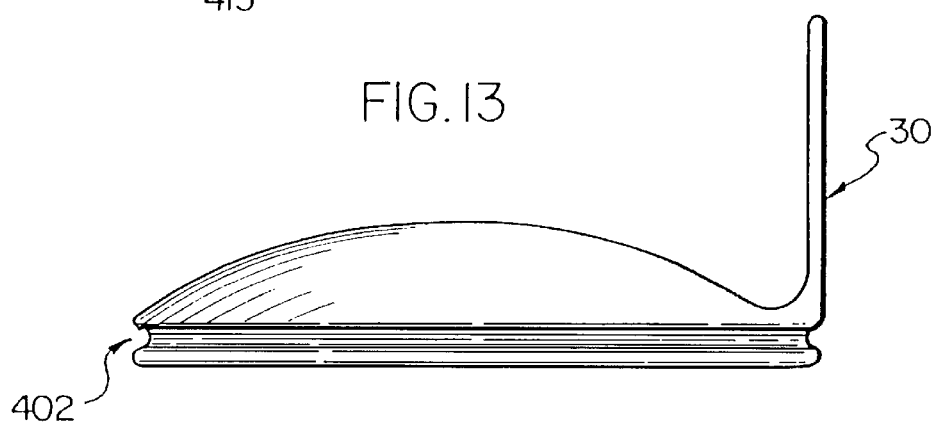
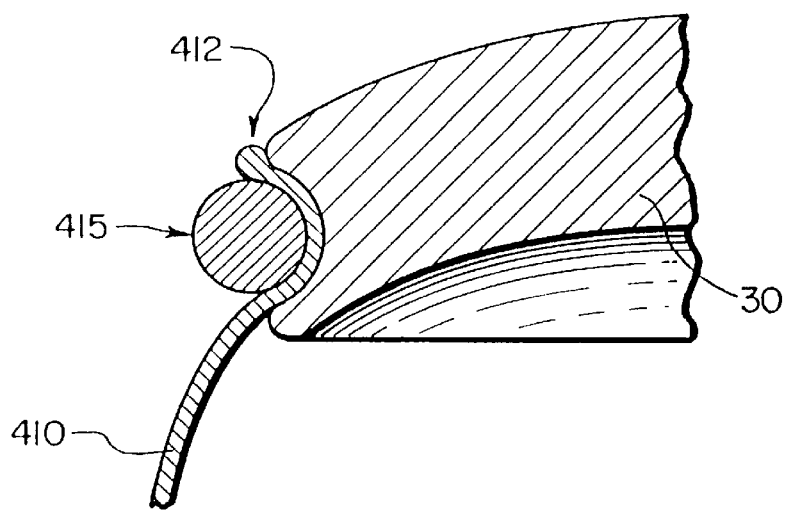

HUMAN SPINAL DISC PROSTHESIS

This is a divisional of U.S. patent application Ser. No. 08/681,230, filed Jul. 22, 1996, U.S. Pat. No. 5,674,296, and which is a continuation-in-part of U.S. patent application Ser. No. 08/339,490, filed Nov. 14, 1994, which is abandoned.

BACKGROUND OF THE INVENTION

This invention relates generally to human prostheses, and especially to spinal column vertebral disc prostheses. The invention also relates to surgical procedures for preparing the patient to receive a vertebral disc endoprosthesis, and for implanting that endoprosthesis in the patient's spine.

The herniation of a spinal disc and the often resultant symptoms of intractable pain, weakness, sensory loss, incontinence and progressive arthritis are among the most common of debilitating processes affecting mankind. If a patient's condition does not improve after conservative treatment, and if clear physical evidence of nerve root or spinal cord compression is apparent, and if correlating radiographic studies (i.e., MRI or CT imaging or myelography) confirm the condition, surgical removal of the herniated disc may be indicated. The process of discectomy—as the name implies—involves the simple removal of the disc without attempt to replace or repair the malfunctioning unit. In the United States in 1985, over 250,000 such operations were performed in the lumbar spine and in the cervical spine.

Statistics suggest that present surgical techniques are likely to result in short-term relief, but will not prevent the progressive deterioration of the patient's condition in the long run. Through better pre-operative procedures and diagnostic studies, long-term patient results have improved somewhat. But it has become clear that unless the removed disc is replaced or the spine is otherwise properly supported, further degeneration of the patient's condition will almost certainly occur.

In the mid-1950's and 60's, Cloward and Smith & Robinson popularized anterior surgical approaches to the cervical spine for the treatment of cervical degenerative disc disease and related disorders of the vertebrae, spinal cord and nerve root; these surgeries involved disc removal followed by interbody fusion with a bone graft. It was noted by Robinson (Robinson, R.A.: The Results of Anterior Interbody Fusion of the Cervical Spine, J. Bone Joint Surg., 440A: 1569–1586, 1962) that after surgical fusion, osteophyte (bone spur) reabsorption at the fused segment might take place. However, it has become increasingly apparent that unfused vertebral segments at the levels above and below the fused segment degenerate at accelerated rates as a direct result of this fusion. This has led some surgeons to perform discectomy alone, without fusion, by a posterior approach in the neck of some patients. However, as has occurred in surgeries involving the lower back where discectomy without fusion is more common as the initial treatment for disc herniation syndromes, progressive degeneration at the level of disc excision is the rule rather than the exception. Premature degenerative disc disease at the level above and below the excised disc can and does occur.

Spine surgery occasionally involves fusion of the spine segments. In addition to the problems created by disc herniation, traumatic, malignant, infectious and degenerative syndromes of the spine can be treated by fusion. Other procedures can include bone grafts and heavy duty metallic rods, hooks, plates and screws being appended to the patient's anatomy; often they are rigidly and internally fixed. None provide for a patient's return to near-normal functioning. Though these procedures may solve a short-term problem, they can cause other, longer term, problems.

A number of attempts have been made to solve some of the problems described above by providing a patient with spinal disc prostheses, or artificial discs of one sort or another. For example, Steffee, U.S. Pat. No. 5,031,437, describes a spinal disc prosthesis having upper and lower rigid flat plates and a flat elastomeric core sandwiched between the plates. Frey et al., U.S. Pat. Nos. 4,917,704 and 4,955,908, disclose intervertebral prostheses, but the prostheses are described as solid bodies.

U.S. Pat. Nos. 4,911,718 and 5,171,281 disclose resilient disc spacers, but no inter-connective or containing planes or like elements are suggested, and sealing the entire unit is not taught.

It is the primary aim of the present invention to provide a vertebral disc endoprosthesis which will perform effectively and efficiently within a patient's spine over a long period of time, and which will not encourage degeneration of or cause damage to adjacent natural disc parts.

It is another object to provide a vertebral disc endoprosthesis which does not require pins or other common mechanical hinge elements, yet which permits natural motion of the prosthetic parts and the adjacent natural anatomy.

It is a related objective to provide a new vertebral disc endoprosthesis surgical procedure which will decrease post-operative recovery time and inhibit post-operative disc, vertebral body and spinal joint degeneration.

It is yet another object to provide a method of installing the endoprosthesis so as to accurately mate the endoprosthesis with an adjacent specifically formed bone surface. An associated object is to provide an endoprosthesis which will encourage bone attachment to, and growth upon, adjacent outer surfaces of the endoprosthesis.

Yet another object is to provide a vertebral endoprosthesis in which the parts are non-oncogenic.

Still another object is to provide a vertebral disc endoprosthesis having a resilient element to accommodate shocks and other forces applied to the spine.

Another object is to provide a highly effective vertebral endoprosthesis which includes several disc endoprostheses and one or more prosthetic vertebral bodies. A related object is to provide these elements in a pre-assembled array for implantation in a patient.

SUMMARY OF THE INVENTION

To accomplish these objects, the invention comprises a resilient body formed of a material varying in stiffness from a relatively stiff exterior portion to a relatively supple central portion. A concaval-convex means at least partly surrounds that resilient body so as to retain the resilient body between adjacent vertebral bodies of a patient's spine. If medical considerations so indicate, several disc endoprostheses can be combined with one or more endoprosthetic vertebral bodies in an entire assembly.

To implant this endoprosthesis assembly, information is obtained regarding the size, shape, and nature of a patient's damaged natural spinal discs. If one or more of the patient's vertebral bodies also require replacement, information about those bodies is also obtained. Thereafter, one or more prosthetic disc units and interposed prosthetic vertebral body units are constructed and preassembled in conformity with that information. Finally, the completed and conformed prosthetic disc and vertebral body assembly is implanted in the patient's spine.

Other objects and advantages of the invention will become apparent upon reading the following detailed description and upon reference to the drawings. Throughout the drawings, like reference numerals refer to like parts.

BRIEF DESCRIPTION OF THE DRAWINGS

FIG. 11 is a top view of a retainer means for use with a vertebral disc endoprosthesis;

FIG. 12 is a sectional view taken substantially in the plane of line 12—12 of FIG. 11;

FIG. 13 is a side view of a vertebral disc endoprosthesis having a groove for receiving the retainer means; and FIG. 14 is a cross-sectional view of the retainer means in use.

DETAILED DESCRIPTION

While the invention will be described in connection with a preferred embodiment and procedure, it will be understood that it is not intended to limit the invention to this embodiment or procedure. On the contrary, it is intended to cover all alternatives, modifications, and equivalents as may be included within the spirit and scope of the invention as defined by the appended claims.

Figure 1:
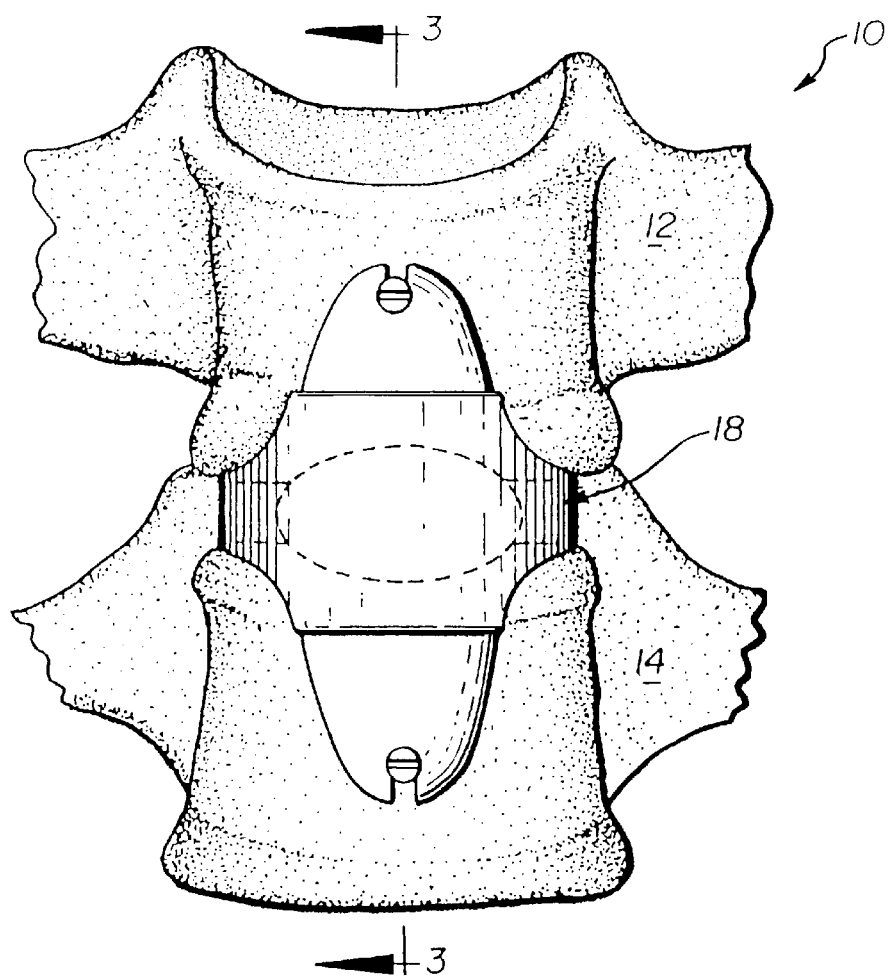
FIG. 1 is a fragmentary vertical view of a portion of a human spine in which is installed a novel vertebral disc endoprosthesis embodying the present invention.
Figure 2:
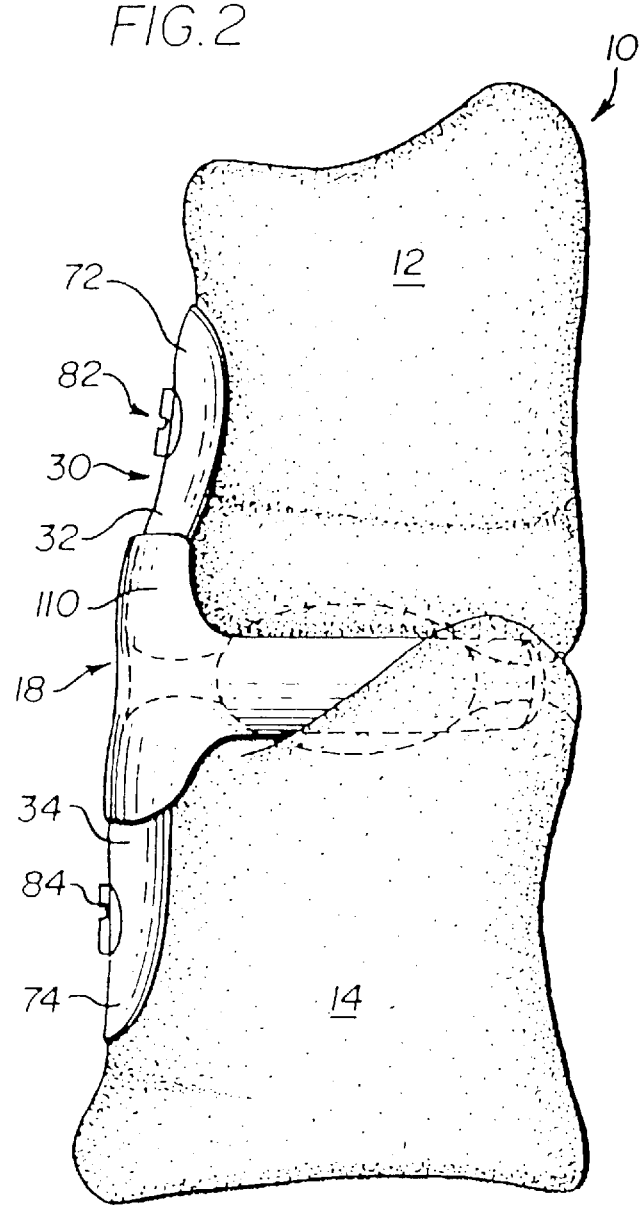
FIG. 2 is a fragmentary side elevational view similar to FIG. 1 showing the elements of a patient's spine and having a novel vertebral disc endoprosthesis embodying the present invention installed therein.
Figure 3:
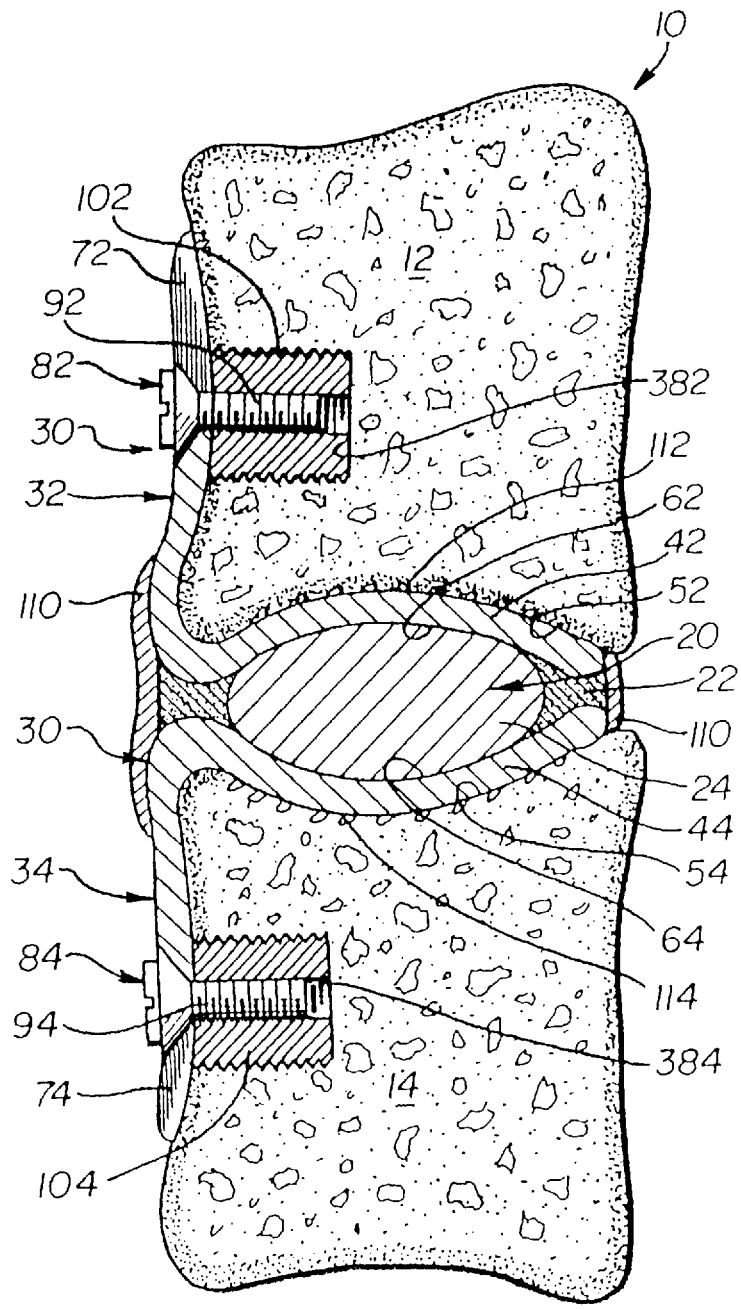
FIG. 3 is a sectional view taken substantially in the plane of line 3—3 in FIG. 1.
Figure 4:
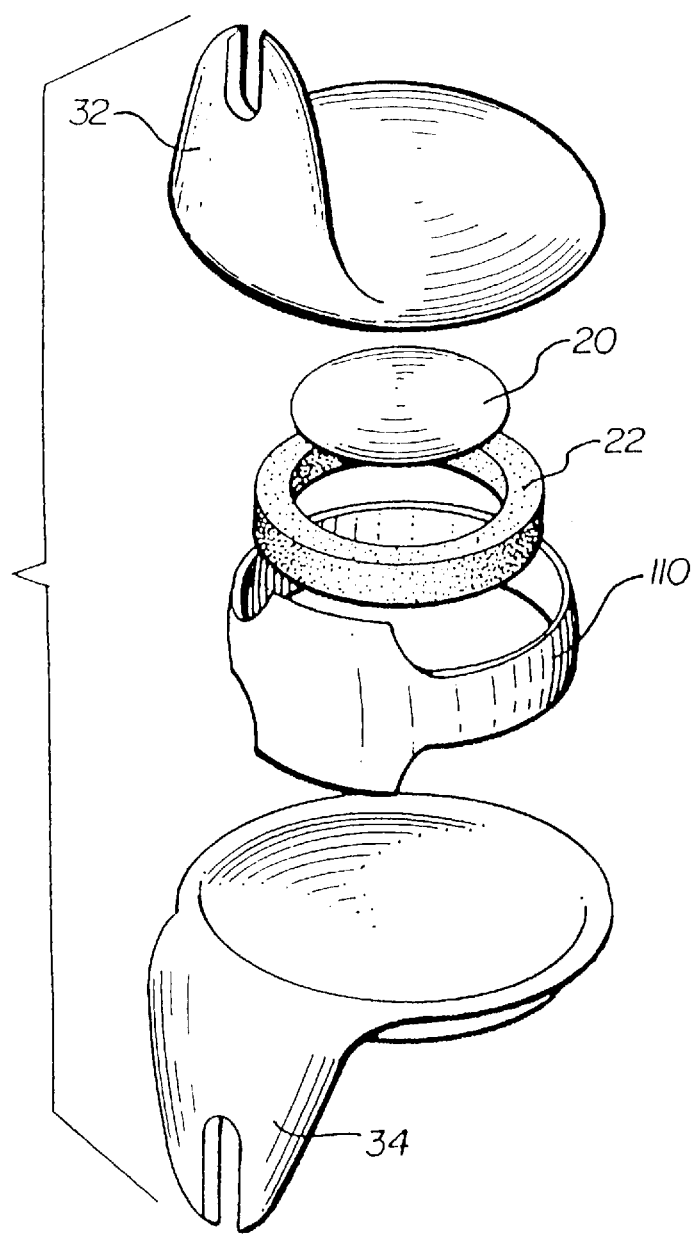
FIG. 4 is an exploded view of the novel vertebral disc endoprosthesis.

Turning more specifically to FIGS. 1–3, a portion of a human spine 10 is shown. The illustrated spine 10 has been subjected to a discectomy surgical process. To discourage degeneration of or damage to the natural vertebral bodies 12 and 14 and their respective facet joints, in accordance with the invention, a vertebral disc endoprosthesis 18 is affixed between the adjacent natural vertebral bodies 12 and 14. Here this vertebral disc endoprosthesis 18 comprises a resilient disc body 20 having a relatively stiff annular gasket exterior portion 22 and a relatively supple nuclear central portion 24. The annular gasket 22 can be formed from a suitable biocompatible elastomer of approximately 90 durometer hardness and the nuclear central portion 24 can be formed from a softer biocompatible elastomeric polymer of approximately 30 durometer hardness.

Concaval-convex means 30 surround the resilient body 20 to retain the resilient body 20 between the adjacent natural vertebral bodies 12, 14 in a patient's spine 10. To this end, as shown in FIG. 3, the concaval-convex means 30 comprise two generally L-shaped supports 32 and 34. The supports 32, 34 each have confronting first concaval-convex legs 42, 44, each leg being of relatively constant cross-sectional thickness. Each leg 42, 44 has an outer convex surface 52, 54 for engaging the adjacent bone of the natural vertebral bodies 12, 14. Corresponding inner concave surfaces 62, 64 in confronting array retain the resilient body 20 in its illustrated compressive force shock-absorbing position. These supports 32 and 34 can undergo principle movement away from one another, but only limited secondary translational, rotational and distractional motion will occur. Each support 32, 34 has a second wing or leg 72, 74 extending generally perpendicularly to the first legs 42, 44 respectively, and adapted for affixation to the adjacent bone structure. To carry out aspects of the invention described below, this affixation is effectively accomplished by cannulated screw devices 82, 84 which may be of a biodegradable type manufactured by Zimmer of Largo, Fla. Each device 82, 84 comprises a screw 92, 94; and a screw anchor 102, 104 adapted to threadably receive the screw extends radially into and seats within the bone structure 12, 14 as especially shown in FIG. 3.

To discourage and prohibit migration of fluids between the endoprosthesis 18 and adjacent parts of the anatomy, a seal member 110 is attached to the supports 32, 34 so as to surround the resilient body 20 comprised of the gasket 22 and nucleus 24, in accordance with another aspect of the invention. Here, this seal member 110 comprises a flexible sheet material having a multiplicity of pores. Preferably, the pores are from about 5 microns to about 60 microns in size. A flexible, strong polymer sheet material from which this seal is formed can be a Kevlar-like material, or it can be Goretex-like material, or other appropriate biocompatible material, such as polyether, polyurethane, or polycarbonate urethane membranes, can be used. Kevlar material is offered by the E. I. DuPont de Nemours Company of Wilmington, Delaware and Goretex material is offered by the W. T. Gore Company of Flagstaff and Phoenix, Arizona. Known sealing material can be applied to the flexible sheet material so as to render the flexible sheet material substantially impervious to the passage of any fluid. A watertight seal is perfected when the seal 110 is glued or otherwise affixed to the legs 42, 44 and mediate portions of the legs 72, 74 as suggested in FIGS. 1—3.

In an alternative embodiment, the watertight seal between the endoprosthesis 18 and adjacent parts of the anatomy can be provided by developing a groove 402 completely encircling the periphery of each of the legs 42, 44. Only one of the grooves is shown in FIG. 13. In this embodiment, the seal member 410 is provided with a beaded edge 412 for each groove. Additionally, a retaining band 415 is provided for each groove to retain the seal member 410 in grooves 402. The retaining bands 415 can be in the form of a biocompatible monofilament wire of, for example, stainless steel or titanium, a synthetic polymer cable or a braided wire cable. As shown in FIG. 11, each retaining band is crimped anteriorly by a crimping sleeve 420. Of course, more than one crimping sleeve may be used, if necessary. Although one sealing arrangement consisting of the groove, beaded edge and retaining band is shown in FIG. 14, it should be understood that the sealing arrangement on the concaval-convex leg of the other support is identical in design and function.

In use, the seal member 410 is placed about the concaval-convex means 30. The retaining bands 415 are then placed adjacent to the respective groove 402 and crimped anteriorly, thereby fitting the bands into the grooves. Each beaded edge 412 prevents the slipping of the seal member underneath the retaining band. Thus, the retaining band, the groove and the beaded edge all cooperate to provide a water-tight seal to prevent the migration of fluids between the endoprosthesis 18 and adjacent parts of the anatomy. Glue can also be used to affix the seal member to the concaval-convex means 30 as a supplemental means for perfecting the seal.

In accordance with another aspect of the invention, the supports 32, 34 are formed of a biocompatible metal which may contain chromium cobalt or titanium. Surface roughening or titanium beading 112, 114 on the exterior surfaces 52, 54 of legs 42, 44 encourages positive bonding between the adjacent bone and the convex surfaces 52, 54.

Figure 9:
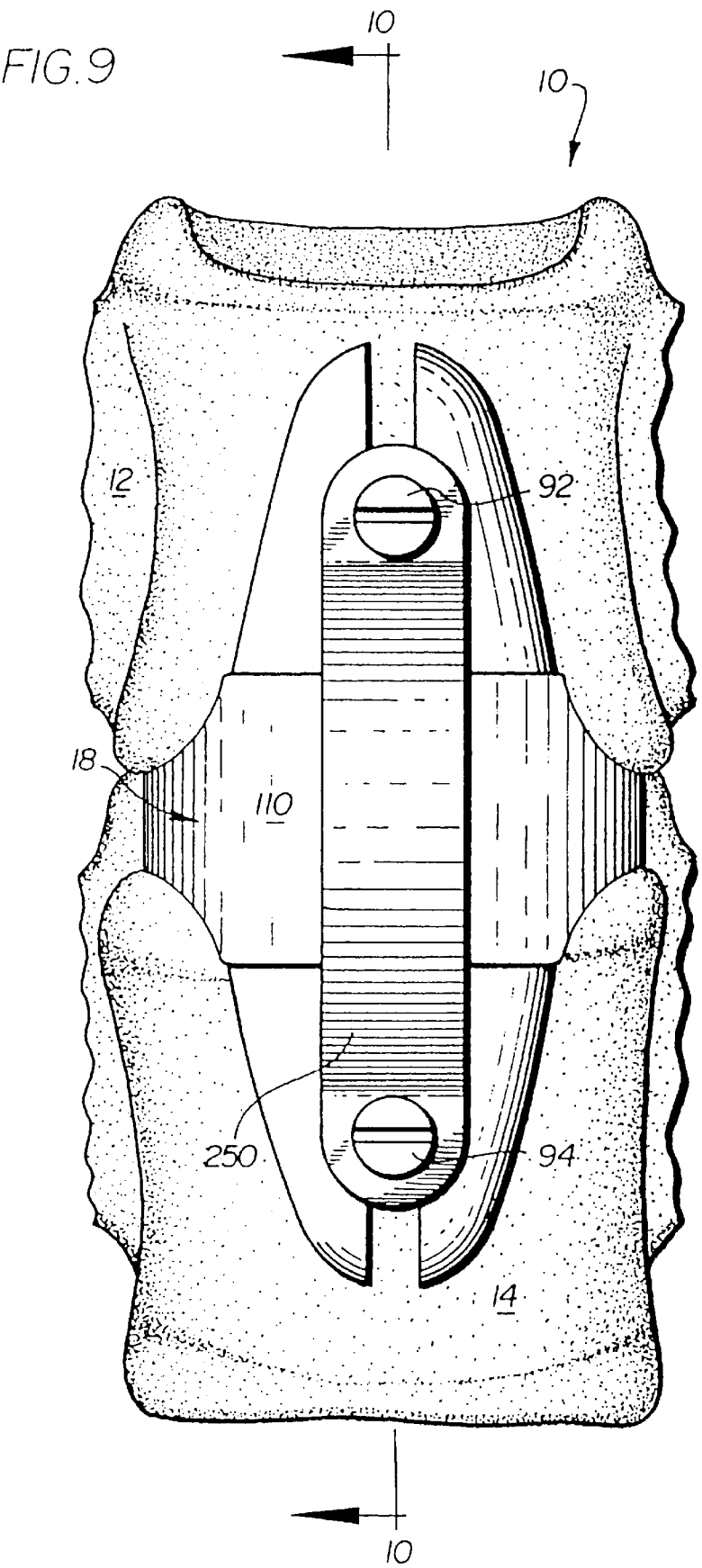
FIG. 9 is a fragment vertical view, similar to FIG. 1, of a portion of a human spine in which is installed a variant form of the novel vertebral disc endoprosthesis the variant form having a prosthetic longitudinal ligament.
Figure 10:
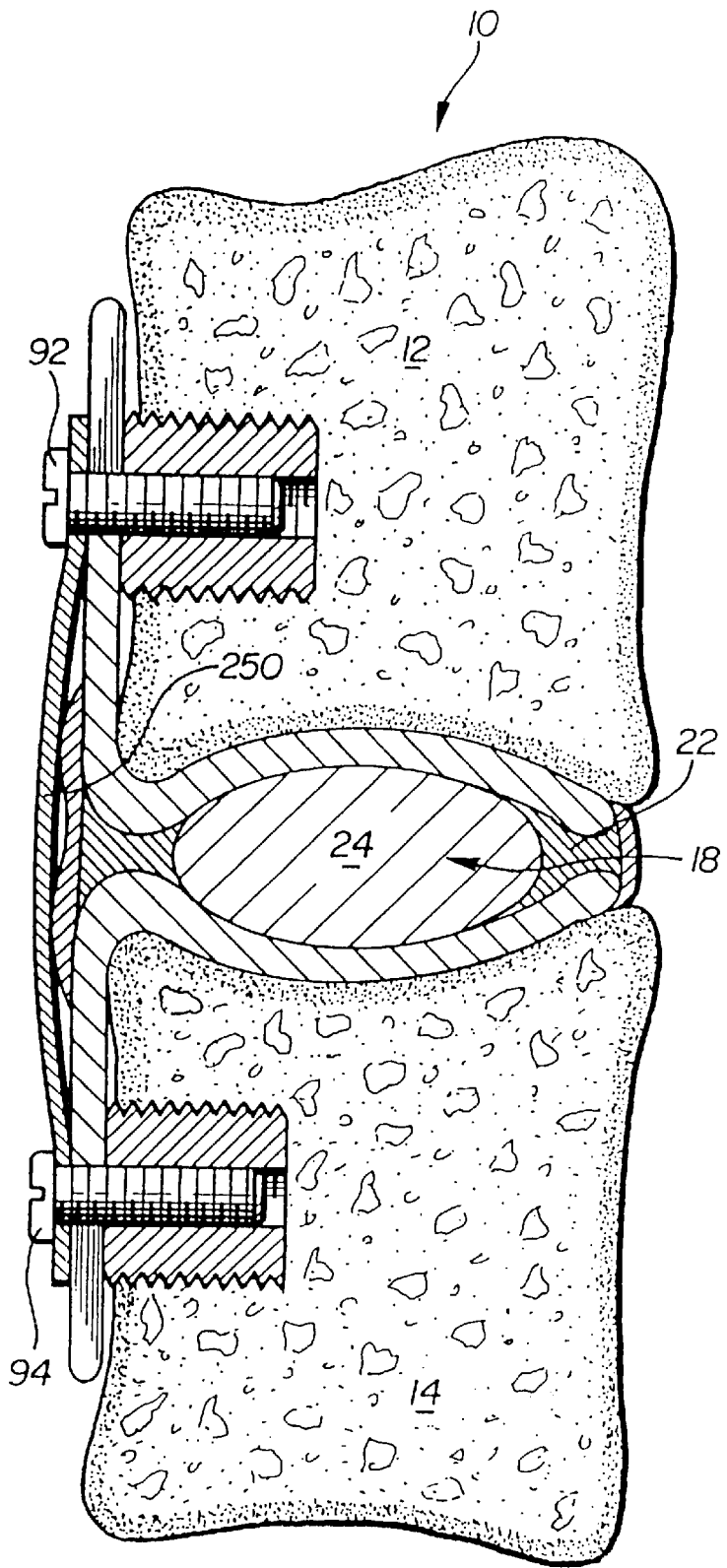
FIG. 10 is a sectional view taken substantially in the plane of line 10—10 in FIG. 9.

As suggested in FIGS. 9 and 10, a prosthetic longitudinal ligament 250 can be connected between the screws 92, 94 to limit motions between elements of the spine 10 in the area where the endoprosthesis 18 is implanted. This strap 250 may be made of the Kevlar-like material or the Goretex-like material described above, or it may be made of any other strong biocompatible material.

Figure 5:
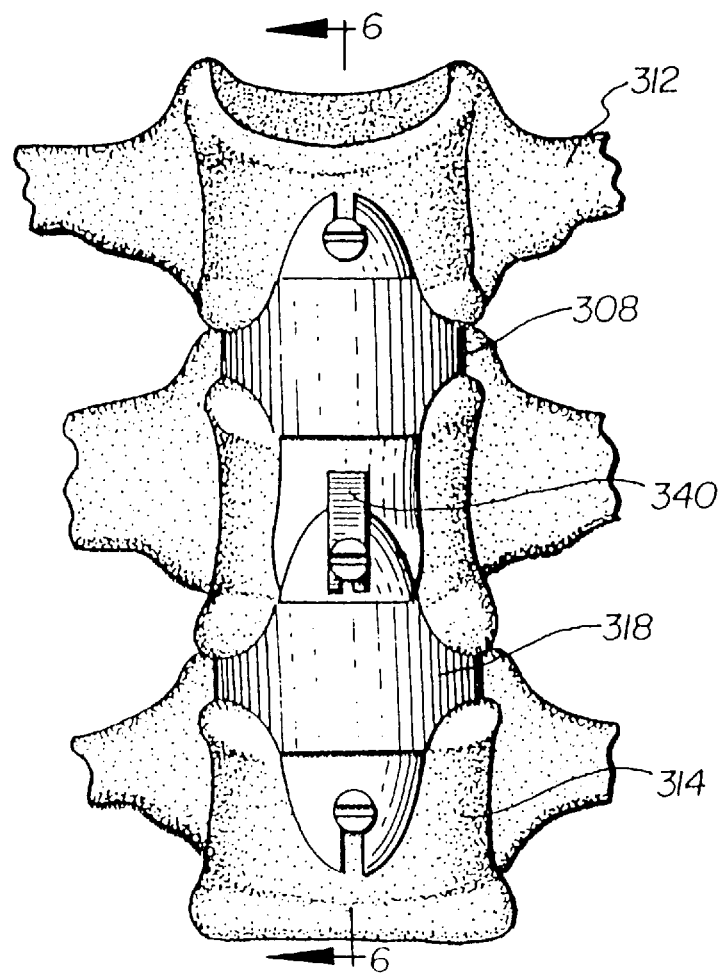
FIG. 5 is a vertical fragmentary view of a patient's spine similar to FIG. 1, but showing a series of novel disc endoprosthesis units installed in the spine and interconnected to one another.
Figure 6:
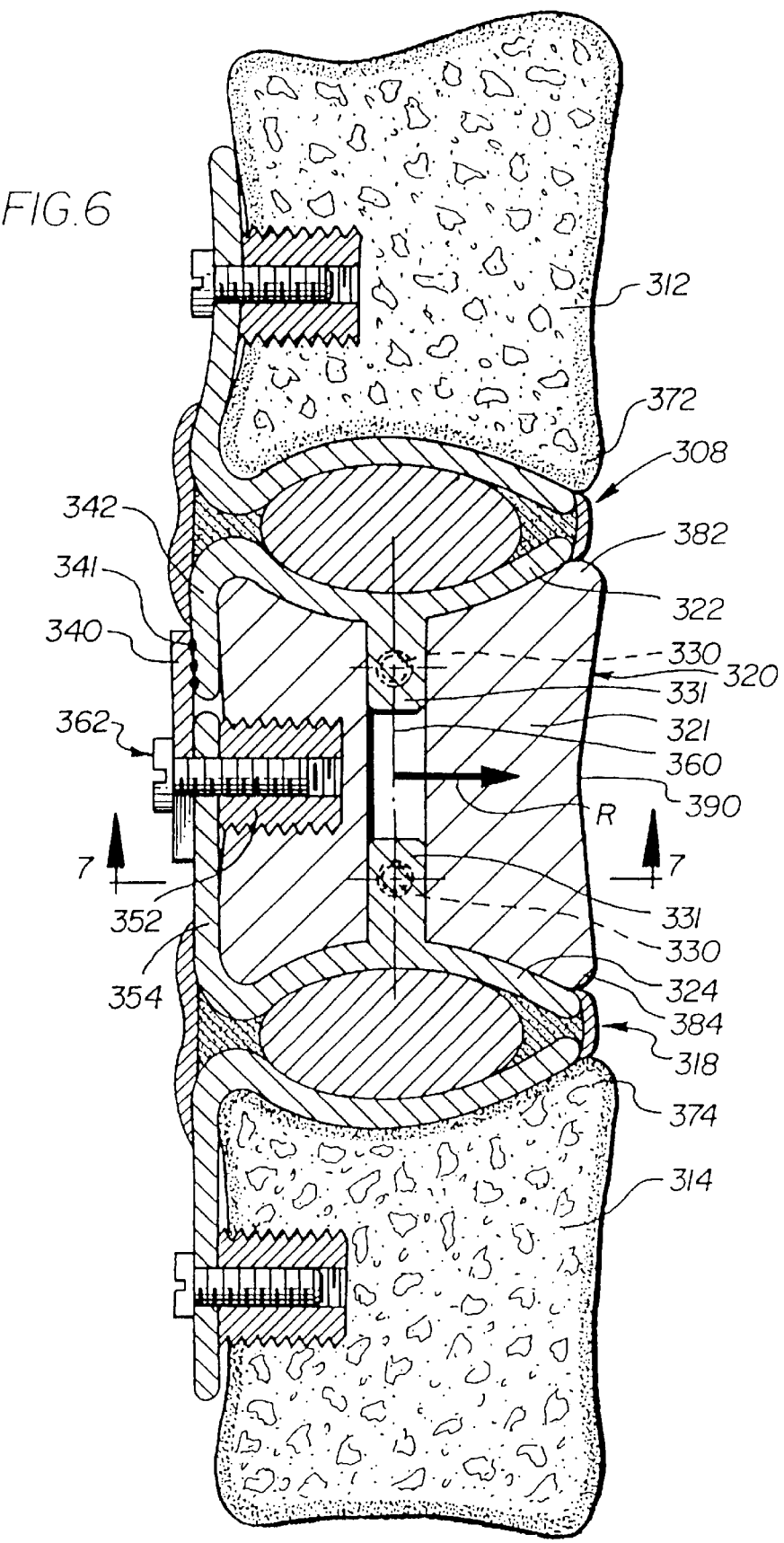
FIG. 6 is a fragmentary sectional view of a patient's spine similar to FIG. 3 and taken along line 6—6 in FIG. 5, but showing a natural upper vertebral body, and upper endoprosthetic disc; an adjacent endoprosthetic vertebral body; a second or lower endoprosthetic disc; and a second or lower natural vertebral body; p
Figure 7:
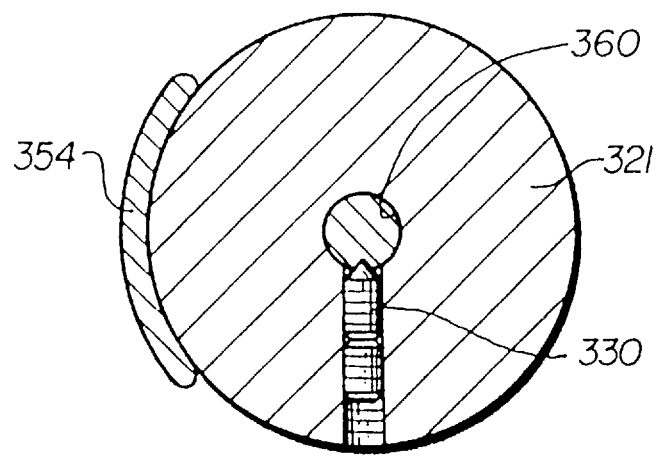
FIG. 7 is a sectional view taken substantially in the plane of line 7—7 of FIG. 6.
Figure 8:
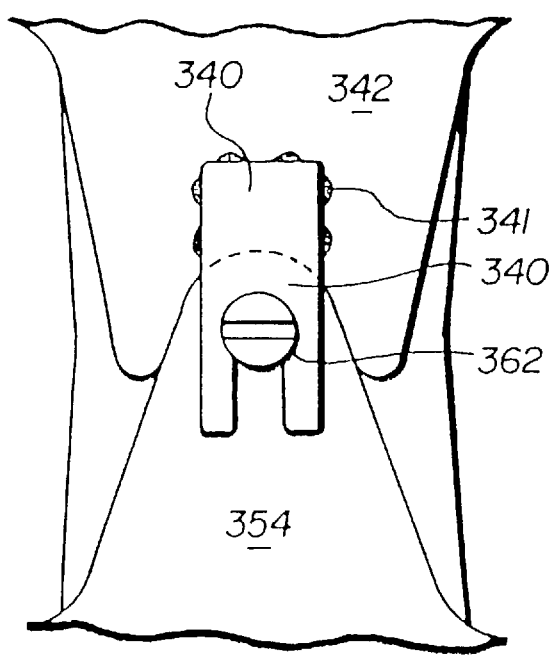
FIG. 8 is a fragmentary side elevational view of the assembly shown in FIG. 6.

In accordance with another aspect of the invention, multiple endoprosthetic disc units can be placed in series with a straddling interlock appendage providing stability and fixation as shown in FIG. 5. Entire portions of a patient's spine can be replaced by a series of interconnected endoprosthetic vertebral bodies and endoprosthetic disc units. FIGS. 6–8 show an upper natural vertebral body unit 312 to which an upper endoprosthetic body 308 has been attached. A lower natural vertebral body 314 has attached, at its upper end, an endoprosthetic disc unit 318. Between these endoprosthetic disc units 308 and 318 is an endoprosthetic vertebral body 320. As suggested by FIG. 7, the endoprosthetic vertebral body 320 need not be irregularly shaped in cross sectional aspect; rather, manufacturing processes may suggest that it have a circular cross-sectional shape. As show in FIGS. 6 and 8, this endoprosthetic vertebral body 320 comprises a titanium element 321, to which are attached the preformed upper and lower endoprosthetic vertebral body upper and lower concaval-convex elements 322, 324. Each concaval-convex element 322, 324 is attached to the prosthetic vertebral body 320, as shown in FIG. 7, by extending set screws 330 through the titanium vertebral body 321 into a stem-like projection 331 extending from each of the concaval-convex elements 322, 324. A hole 360 in the body 320 accommodates the stem-like projections 331 of the concaval-convex elements 322 and 324. The stem-like projection 331 of the concaval-convex elements 322 and 324 is used only in conjunction with a prosthetic vertebral body implant construction 320.

An ear 340 is affixed, as by weldments 341, to a leg 342 extending from a concaval-convex element 322 as illustrated in FIGS. 6 and 8. An anchor 352 can be threaded into the endoprosthetic vertebral body 320, and a screw 362 can be turned into the anchor 352 so as to rigidly assemble the leg 342 to a leg 354 extending from the lower endoprosthetic disc unit 318.

The upper disc endoprosthesis 308, the endoprosthetic vertebral body 320, and the lower disc endoprosthesis 318 can all be assembled and interconnected as a unit before implantation in a patient's body when indicated.

As also suggested in FIG. 6, the annular corners 372, 374 of natural vertebral bodies 312, 314 each can extend irregularly radially outwardly of the adjacent disc endoprosthesis 308, 318. However, the corners 382B, 384B of the prosthetic vertebral body 320 do not generally extend significantly outside those disc units 308, 318, thus discouraging vertebral body engagement with and consequent abrasion or other damage to adjacent portions of the patient's natural anatomy. Preferably the endoprosthetic vertebral body 320 is not exactly right cylindrical in shape, but is rather slightly biconical; that is, the endoprosthetic vertebral body 320 has a waist 390 of minimum radius R at an axial medial point as suggested in FIG. 6.

According to yet another aspect of the invention, novel surgical procedures permit effective and permanent installation of the endoprosthetic vertebral body 320 and associated parts. First, a surgeon or medical technician develops information about the size, shape and nature of a patient's damaged vertebral body or bodies from radiographs, CT and/or MRI scans, noting specifically the anterior-posterior and lateral dimensions of the end plate of each involved vertebral body and the vertical height of the anterior aspect of each involved vertebral and/or proximate vertebral body and vertical height of the mid portion of involved and proximate relatively normal intervertebral disc spaces. This information is transmitted by telephone, computer datalink or documentary transport to a specialized laboratory. That laboratory constructs one or more prosthetic assemblies of the sort shown in FIG. 6 in conformity with the received information and this disclosure. Each of the assemblies can include a prosthetic vertebral body 321, and at each body end is a prosthetic disc 308,318. Each prosthetic disc unit comprises, in turn, the concaval-convex elements 30; the resilient body 20 interposed between the concaval-convex elements; and the seal unit 110 secured around the interior legs and resilient body. Thereafter, the completed and conformed assembly is implanted in the patient's spine 10.

When the unit or units have been received and the patient properly prepared, the damaged natural spinal disc or discs and vertebral body or bodies are removed and the adjacent spinal bone surfaces are milled or otherwise formed to provide concave surfaces to receive the confronting convex surfaces 52, 54. Thereafter, the disc units and vertebral body are installed in the patient's spine.

To accurately locate the concaval-convex surfaces in the patient's spine, holes 382A, 384A (FIG. 3) are precisely located and then formed in the bone structure using a measuring instrument centered in the evacuated natural intravertebral disc space. These holes are then tapped to form female threads therein. When the threads have been formed, the anchors 102, 104 are implanted in the respective tapped holes, thereby creating reference points located precisely with respect to the patient's spine. After the holes have been formed and the anchors 102, 104 implanted, a bone surface milling jig (not shown) is affixed to the anchors 102, 104 and the desired concave surfaces of predetermined shape are formed on the inferior and superior surfaces of the opposing vertebral bodies using one of a selection of predetermined milling head or bit sizes. Thereafter, the bone milling jig is removed and the concaval-convex elements 52, 54 identical in shape to the milled surfaces 112, 114 are inserted between the distracted milled vertebral bodies 12, 14. The distraction device is then moved. The concaval-convex structures are then attached by the same anchors 102, 104 to the bone, thus insuring a precise and stable mate between the bone surfaces and the convex surfaces 52, 54.

If necessary, a damaged implanted nucleus and/or gasket 24 can be removed and replaced. This can be accomplished by slitting the seal 110; removing the annular gasket 24 and damaged nucleus 22, and replacing them with new, undamaged elements. Thereafter, the seal 110 can be re-established by suturing or gluing closed the slit seal.

We claim:

1. A method of endoprosthetic discectomy surgery comprising the steps of receiving information about the size, shape and nature of a patient's damaged natural spinal vertebral bodies and discs from radiographs, CT and/or MRI scans or other imaging devices specifically determining the anterior-posterior and lateral dimensions of each involved vertebral body, the vertical height of the anterior aspect of each involved vertebral and/or proximate vertebral body, and the vertical height of the mid-portion of the involved and proximate normal intervertebral disc spaces, thereafter constructing one or more prosthetic vertebral body units and prosthetic disc units in conformity with the received information, each prosthetic disc unit including confronting L-shaped concaval-convex elements and a resilient body interposed between the concaval-convex elements; and an endoprosthetic vertebral body interposed between and engaging the adjacent disc units; and thereafter implanting the completed and conformed construction in the patient's spine.

2. A method according to claim 1 including the step of constructing a plurality of prosthetic disc units and further including the step of attaching the disc units to an endoprosthetic vertebral body prior to the step of supplying the assembly to the surgeon.

3. A method according to claim 1 further including the steps of surgically milling spinal bone surfaces with concave surfaces to receive confronting convex surfaces of the concaval-convex elements, and installing at least one disc unit having concaval-convex elements with said convex surfaces in the patient's spine.

4. A method of surgery comprising the steps of removing a vertebral disc from a patient's spine, forming holes at precisely predetermined locations in bone structure adjacent the location of the removed disc, tapping the holes to form a female thread in each hole, and threadably implanting an anchor into each tapped hole, thereby creating reference points located precisely with respect to the patient's spine, forming concave surfaces in adjacent spinal bone, and inserting between the formed bone surfaces a vertebral disc endoprosthesis including confronting concaval-convex supports, each support having an exterior convex surface adapted to mate with the adjacent formed concave spinal bone surface, the endoprosthesis further including a resilient body element interposed between the concaval-convex supports, and thereafter affixing the concaval-convex supports to the adjacent bone.

5. A method of surgery according to claim 4 further including the step of temporarily locating a bone surface milling jig at the site of the removed vertebral disc by means of said anchors prior to implanting said disc endoprosthesis.

6. A method of surgery according to claim 4 further including the steps of attaching a screw to each concaval-convex support and screwing said screw into the implanted anchor.

7. A method of surgery according to claim 4 further comprising the steps of identifying a damaged resilient nucleus body element or annular gasket in an implanted endoprosthesis, removing said damaged nucleus body element or annular gasket from the endoprosthesis and inserting a new, undamaged nucleus body element or annular gasket into the endoprosthesis without removing the concaval-convex supports from the patient's spine.

8. A method of spinal surgery comprising the steps of forming mounting holes in one or more vertebral bodies of a patient's spine; utilizing said mounting holes to mount a bone mill on a patient's spine; milling confronting bone surfaces on and in the patient's spine to a predetermined surface shape; removing said mill; and thereafter mounting a vertebral disc endoprosthesis having a predetermined outer surface shape by means of the original mounting holes so that outer surfaces of the vertebral disc endoprosthesis mate precisely with the previously milled bone surfaces.

9. A method of endoprosthetic discectomy surgery comprising the steps of receiving information about the size, shape and nature of a patient's involved and proximate normal natural spinal vertebral bodies and natural spinal vertebral discs from known imaging devices, thereafter constructing at least one vertebral disc endoprosthesis comprising a resilient disc body and concaval-convex elements at least partly surrounding the resilient disc body, removing at least the involved, natural spinal discs from the patient's spine, forming concave surfaces in adjacent spinal bone, and thereafter implanting the vertebral disc endoprosthesis in the patient's spine.

* * * * *